United States Patent
Decker et al.

(10) Patent No.: US 10,864,172 B2
(45) Date of Patent: Dec. 15, 2020

(54) TRANSDERMAL PATCH FOR OIL DELIVERY

(71) Applicant: Chemsultants International Inc., Mentor, OH (US)

(72) Inventors: Berryinne Decker, Macedonia, OH (US); Keith Muny, Rocky River, OH (US); Gary Avalon, Painesville, OH (US); Brian Buehner, Mentor, OH (US)

(73) Assignee: CHEMSULTANTS INTERNATIONAL INC., Mentor, OH (US)

( * ) Notice: Subject to any disclaimer, the term of this patent is extended or adjusted under 35 U.S.C. 154(b) by 0 days.

(21) Appl. No.: 16/360,654

(22) Filed: Mar. 21, 2019

(65) Prior Publication Data

US 2020/0030250 A1 Jan. 30, 2020

Related U.S. Application Data

(60) Provisional application No. 62/703,113, filed on Jul. 25, 2018.

(51) Int. Cl.
*A61K 9/70* (2006.01)

(52) U.S. Cl.
CPC .................... *A61K 9/7084* (2013.01)

(58) Field of Classification Search
None
See application file for complete search history.

(56) References Cited

U.S. PATENT DOCUMENTS 5,718,913 A * 2/1998 Dhuique-Mayer .......................... A61N 1/0448
424/449
5,773,022 A * 6/1998 Nyqvist-Mayer ........................... A61F 13/0276
424/443

* cited by examiner

*Primary Examiner* — Melissa S Mercier
(74) *Attorney, Agent, or Firm* — Fay Sharpe LLP

(57) ABSTRACT

A transdermal patch is provided for use during oil delivery to a user's skin. The patch has a first foam member and a second foam member positioned adjacent the first foam member. An adhesive member is attached to the second foam member for securing the patch to a user's skin. A release liner covers and extends across the adhesive member. A gap can be formed between the first foam member and the second foam member and surrounds the first foam member. The first foam member has a thickness which is greater than a thickness of the second foam member.

8 Claims, 3 Drawing Sheets

TRANSDERMAL PATCH FOR OIL DELIVERY

CLAIM OF PRIORITY

This application claims priority from Provisional Application Ser. No. 62/703,113 filed on Jul. 25, 2018, the entirety of which is hereby incorporated by reference.

BACKGROUND OF THE DISCLOSURE

This disclosure relates to transdermal patches. More particularly, it relates to transdermal patches for drug delivery. Transdermal delivery relates to delivery of drugs through the skin into the circulatory system. This method has become an alternative to oral and other kinds of drug delivery. Transdermal delivery also provides the benefits of bypassing first-pass metabolism and provides controlled continuous delivery.

There are two major existing designs of transdermal patches: 1) "drug-in-adhesive patches"; and 2) "drug-in-reservoir, adhesive-separated patches". The "drug-in-adhesive" patches typically include a drug which is mixed into a pressure sensitive adhesive polymer matrix. It is a relatively simple design. There are, however, several disadvantages to this design.

A first disadvantage of the "drug-in-adhesive" patch is there is a thickness/dose limitation. Most pressure sensitive adhesives require the use of solvents. The drying process to remove the solvents limits the thickness of the patch and the subsequent drug dose that can be supplied.

A second disadvantage of the "drug-in-adhesive" patch is potential thermal degradation. That is, some drugs are sensitive to heat. However, heating is a necessary process for making "drug-in-adhesive" patches in order to remove solvent or achieve proper process viscosity. The heating process can lead to drug evaporation and/or chemical degradation.

A third disadvantage of the "drug-in-adhesive" patch is adhesion degradation. Some drugs are used in liquid form. The liquid components of the drugs can eventually lead to the loss of adhesive properties over time, resulting in inadequate adhesion of the patch to the user's skin.

In contrast, the "drug-in-reservoir, adhesive-separated" patch design avoids many of the disadvantages mentioned above. However, the process to make such a reservoir system is fairly complicated and can be expensive. The drugs are usually loaded between a backing layer and a rate-controlling membrane. Then an adhesive layer is used to seal the perimeter of the patch to prevent leakage. This is a fairly complicated and expensive procedure.

Thus, there is a need for a "drug-in reservoir, adhesive separated" patch which can be assembled and used without the complexity of existing patches and which overcomes the above-mentioned difficulties and others while providing better overall results.

SUMMARY OF THE DISCLOSURE

The present disclosure relates to transdermal patches. More particularly, it relates to a "drug-in-reservoir, adhesive-separated" patch design which does not have the complexity of existing patches.

In accordance with another embodiment of the disclosure, the structure can be used for transdermal applications where there is no need to control the dose rate of a drug over time. Since there is no rate controlling membrane, the drug's own ability to penetrate through the dermal layer is relied on to establish the dose rate.

In accordance with another embodiment of the disclosure, the structure can also be used for topical applications for creams, ointments, and skin care agents where the active oil or component acts on the skin surface itself and does not penetrate the dermal layer to enter into the blood stream.

In accordance with one embodiment of the disclosure, the patch is oil loadable and is designed to load and deliver oil to human skin. Liquid agents other than oils may also be used with the patch product.

In accordance with one embodiment of the disclosure, described is a transdermal patch for during delivery, including: a first foam member; a second foam member positioned adjacent the first foam member; an adhesive member attached to the second foam member; and a release liner covering and extending across the adhesive member.

In accordance with another embodiment of the disclosure, a transdermal patch for delivering oil to a user's skin has a first foam member; a second foam member positioned around the first foam member, wherein a gap is formed between the first foam member and the second foam member and surrounds the first foam member; and wherein the first foam member forms an "island" which has a first thickness which is greater than a second thickness of the second foam member. The thicker center foam "island" is then compressed against the user's skin to facilitate disbursement of oil into said user's skin.

In accordance with another embodiment of the disclosure, a method is described for delivery of oil to a user's skin, including the steps of: providing a transdermal patch; removing a release liner from an adhesive side of the patch; loading a desired amount of oil onto a center circular foam island of the patch; reapplying the release liner after about 3 seconds for oil to soak into the foam island; removing the release liner and applying the patch to the user's skin via the adhesive side of the patch; and applying hand pressure to the patch for about 3 to 5 seconds to secure the patch to the user's skin.

In accordance with another embodiment of the disclosure, the center of the patch is a circular polyurethane foam island capable of absorbing up to 500 mg of higher viscosity oils (or 300 mg for lower viscosity oils). The foam island is preferably one inch in diameter.

In accordance with another aspect of the disclosure, the top layer of the patch is a comfortable polyurethane film tape, while the outer ring of the patch is a flexible, polyethylene or polyurethane foam tape, which provides optimal comfort and skin adhesion.

In accordance with another aspect of the disclosure, the outer dimension of the patch is preferably 2 inches×2 inches with ½ inch rounded corners and is about 3-5 mm in thickness.

In accordance with another aspect of the disclosure, all components are of medical grade quality and manufactured to ISO 13485:2016 compliance.

Another embodiment of the disclosure provides that the following oils can be used with the patch: Cannabis oil (CBD, THC, CBG, CBN . . . ); Essential oils (lavender, peppermint . . . ); and Bio-Oils® as well as other suitable liquid agents.

Another aspect of the disclosure is a bandage including an engineered absorbent foam to contain the liquid drug components and a medical-grade adhesive to adhere to the skin.

Another aspect of the disclosure is it provides all the benefits of existing "drug-in reservoir adhesive-separated" designs.

Another aspect of the disclosure is it allows "post-assembly loading". That is, the drugs can be loaded onto the bandage right before packaging.

Yet another aspect of the disclosure is different doses of drug or different variations of formula can be loaded onto the same type of bandage. This greatly reduces the complexity of traditional reservoir patch manufacturing.

Another aspect of the disclosure is that it provides a simple and discrete topical delivery method.

Another aspect of the disclosure is it uses loading technology without the use of heat, thus avoiding decomposing of the oils in the patch.

Another aspect of the disclosure is the patch is water resistant. For example, the patch can be worn while showering over several days, although it is not considered waterproof.

Another aspect of the disclosure is it provides long term transdermal oil delivery.

Another aspect of the disclosure is the patch is sealed to prevent leaking of oil.

Another aspect of the disclosure is the patch is flexible and comfortable to wear.

Another aspect of the disclosure is the patch film provides breathability; that is, the skin underneath the patch can breathe.

Another aspect of the disclosure is the patch can be manually loaded with oil.

Another aspect of the disclosure is the patch can be automatically loaded on a converter machine where the patch is on a first roll and the release liner is on a separate roll.

Still other aspects of the disclosure will become apparent upon a reading and understanding of the following detailed description.

DETAILED DESCRIPTION OF THE DISCLOSURE

The present disclosure includes several preferred embodiments. The embodiments provide several different patch structures. The patch structures, however, provide essentially the same function, except some of the patch structures provide an improved appearance by eliminating release liner wrinkling.

Figure 1:
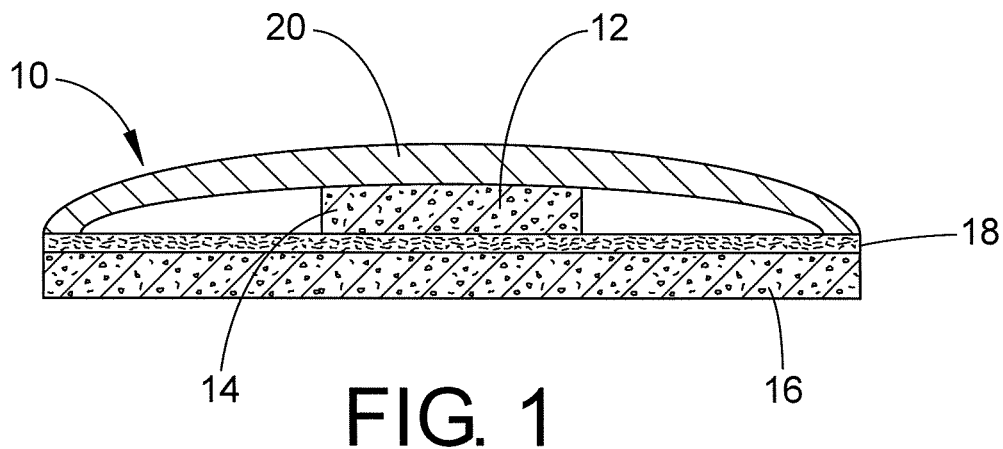
FIG. 1 is a side elevational view in cross-section of a transdermal patch for drug delivery in accordance with a first preferred embodiment of the disclosure.

Referring now to FIG. 1, in accordance with a first preferred embodiment of the disclosure, in a first patch 10, a centrally positioned medical grade foam 12 is selected to absorb liquid drug components such as oil 14. The foam allows the drug or oil to soak in quickly and also holds the drug/oil until the foam contacts the skin of the user. Most bandage gauzes in the market provide reasonable absorbing properties, but do not hold or retain the drug until they contact the skin. The foam 12 used can preferably be a polyurethane foam. The preferred thickness of the foam 12 ranges from 3 mm to 10 mm, with a preferred thickness of about 5 mm.

Another layer of thin foam 16 carries a layer of thin pressure sensitive adhesive (PSA) 18. The thin foam 16 allows the bandage or patch to stretch and also remain intact during wear. Foam 16 can be either polyurethane or polyethylene foam and is preferably about 1 mm to 3 mm in thickness. The patch can be applied to different areas of skin easily. The pressure sensitive adhesive 18 provides effective adhesion to adhere to skin for the desirable length of wear time (such as 4 hours, 8 hours, 24 hours, etc.). Adhesive 18 can be formed from polyurethane film and is preferably about 2 mm thick. In this embodiment, the adhesive 18 adheres the patch to the user's skin and bonds foam 12 and foam 16 together.

A release liner 20 is used to protect the adhesive surface 18 before the adhesive contacts skin. The liner 20 can be made from silicone coated LDPE (Low Density Polyethylene) and is about 2 mils thick. Once release liner 20 is removed, adhesive 18 is pressed against the user's skin to secure the patch.

Figure 3A:
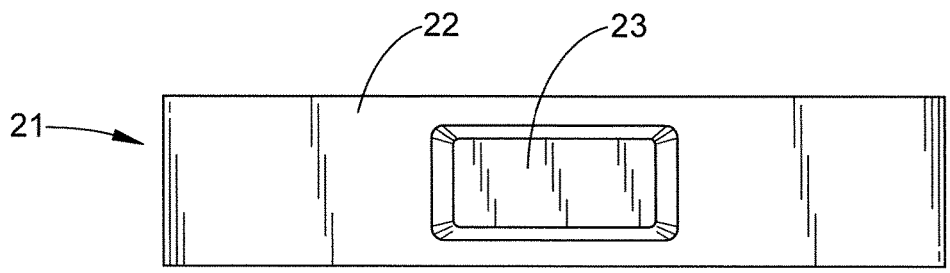
FIG. 3A is a top plan view of a patch in accordance with a preferred embodiment of the disclosure.
Figure 3B:
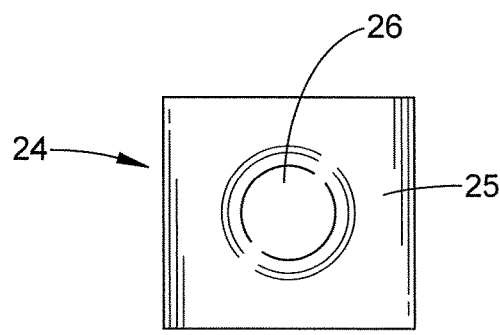
FIG. 3B is a top plan view of another patch in accordance with another preferred embodiment of the disclosure.
Figure 3C:
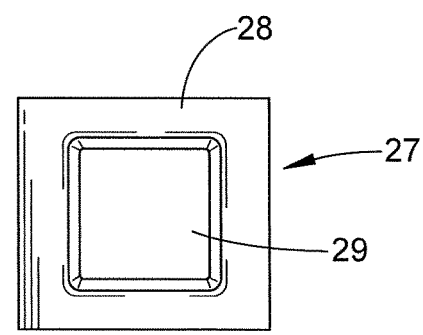
FIG. 3C is a top plan view of another patch in accordance with another preferred embodiment of the disclosure.
Figure 4A:
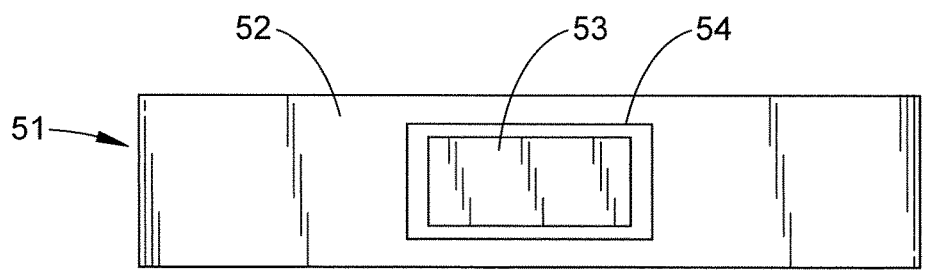
FIG. 4A is a perspective view of another patch in accordance with another preferred embodiment of the disclosure.
Figures 4B, 4C, 4D:
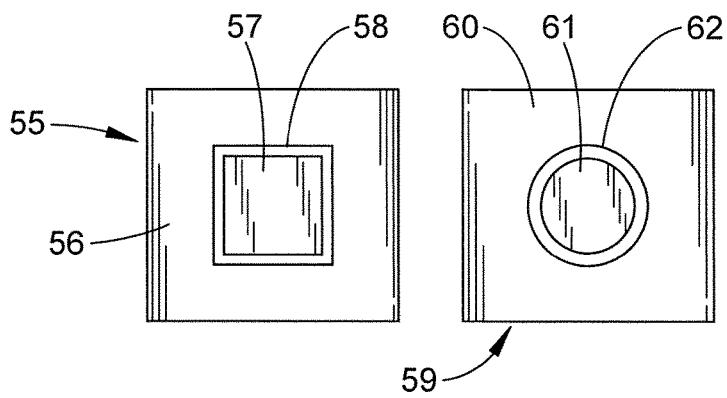
FIG. 4B is a top plan view of another patch in accordance with another embodiment of the disclosure.
FIG. 4C is a top plan view of another patch in accordance with another embodiment of the disclosure.
FIG. 4D is a top plan view of another patch in accordance with another embodiment of the disclosure.

Referring now to FIGS. 3A-3C, several variations of the first preferred embodiment of the patch are shown. For example, a first patch 21 has an elongated rectangular shaped portion 22 with a rectangular foam 23 centrally positioned therein. Second patch 24 has a square shaped portion 25 which has a centrally located circular shaped foam portion 26. Third patch 27 has a square shaped portion 28 with a centrally located square shaped foam portion 29.

Figure 2:
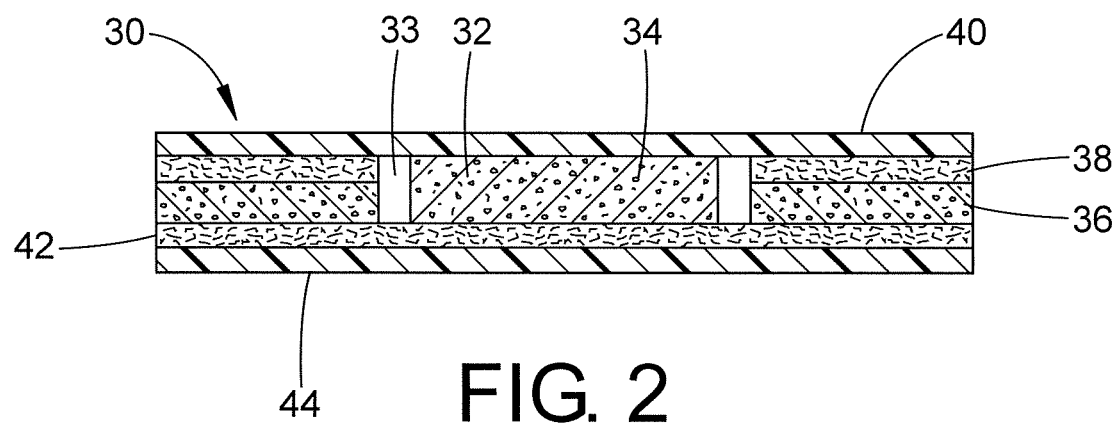
FIG. 2 is a side elevational view in cross-section of a transdermal patch for drug delivery in accordance with a second preferred embodiment of the disclosure.

Referring now to FIG. 2, in accordance with a second preferred embodiment of the disclosure, a "drug-in-reservoir, adhesive separated" patch 30 has two extra components added in addition to all the components for patch 10 in FIG. 1. Patch 30 has a centrally located medical grade foam 32 (such as polyurethane) to absorb liquid drug components such as oil 34. Another layer of foam 36 (such as polyurethane or polyethylene foam), which is preferably thinner than foam 32, carries a layer of pressure sensitive adhesive (PSA) 38 along a surface thereof. Foam 36 essentially surrounds foam 32 and forms a gap 33 therebetween. The gap aids in spacing foam 32 and foam 34 and confines the oil to foam 32. Release liner 40 (such as silicone coated LDPE) is used to protect the adhesive surface 38 before the adhesive contacts the user's skin.

A secondary pressure sensitive adhesive layer (PSA) 42 is used to allow the backing foam 36 and absorbable foam 32 to be attached together. A thin layer of polyurethane film 44 covers the secondary adhesive 42 and holds all the components together.

During use, release liner 40 is removed and adhesive 38 contacts and secures the patch to the user's skin.

FIGS. 4A, 4B, 4C and 4D illustrate several variations of the second preferred embodiment of the disclosure. For example, a first patch 51 has a rectangular shaped portion 52 and a centrally located rectangular foam reservoir portion 53 which forms a "island" which is spaced from the adhesive portion of the patch by gap or area 54 which surrounds foam portion 53. Second patch 55 has a square shaped portion 56 and a centrally located square shaped foam reservoir portion 57 which forms an "island" which is spaced from the adhesive portion of the patch by area or gap 58 which surrounds foam portion 57. Third patch 59 has a square shaped portion 60 and a centrally located circular-shaped foam reservoir portion 61 which forms an "island" which is spaced from the adhesive portion of the patch by area or gap 62 which surrounds foam portion 61. Fourth patch 63 has a round shaped portion 64 and a round shaped foam portion 65 which forms an "island" which is spaced from the adhesive portion of the patch by area or gap 66 which surrounds foam portion 65.

Figure 5:
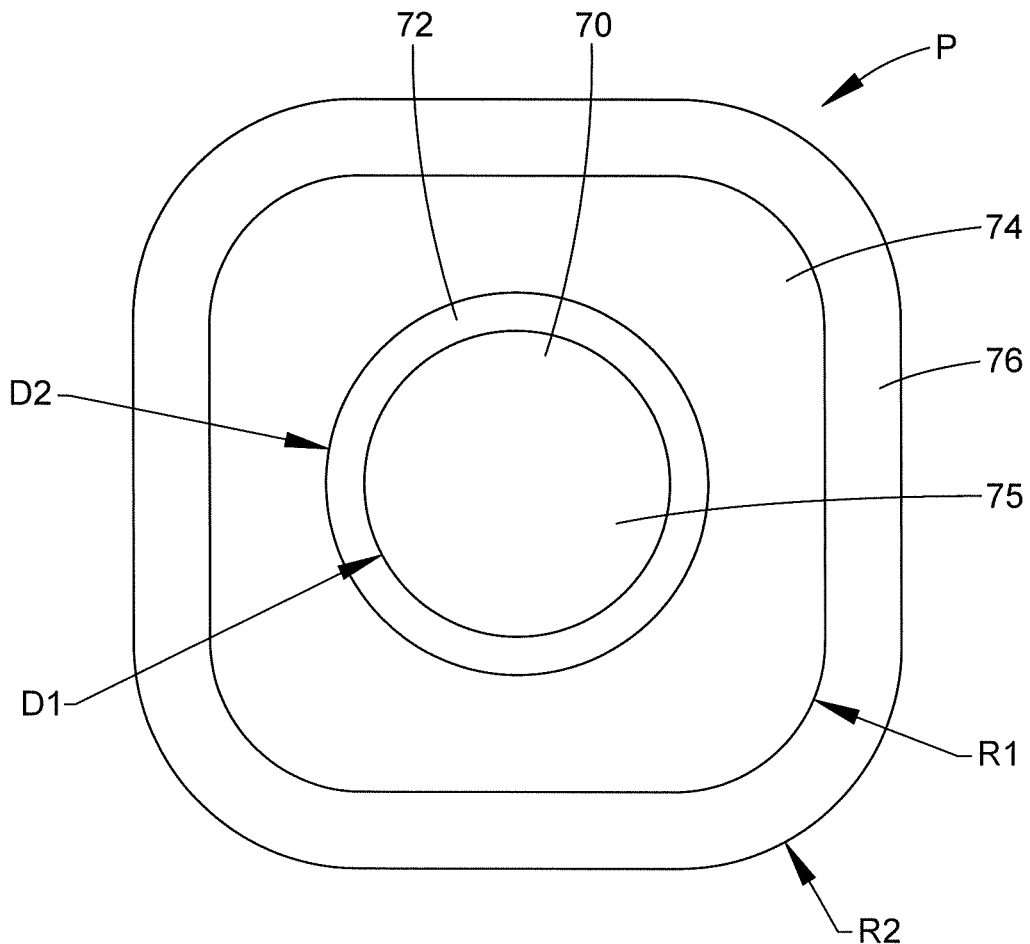
FIG. 5 is a top plan view of a patch with a center foam island in accordance with another preferred embodiment of the disclosure.
Figure 6:
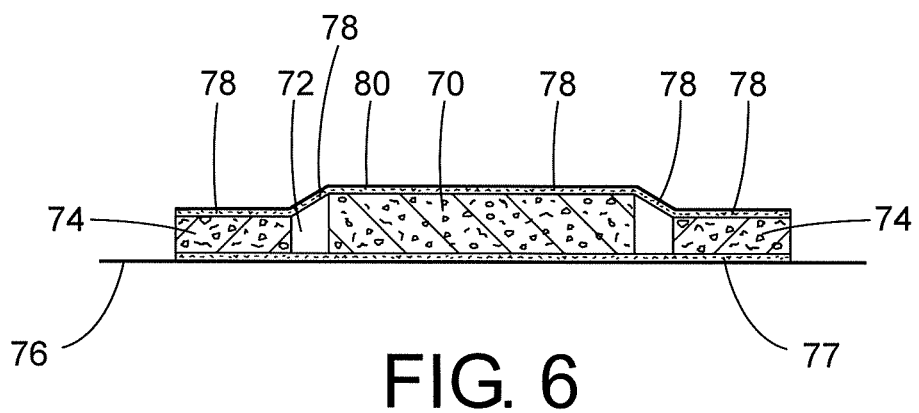
FIG. 6 is a side elevated view in cross section of the patch of FIG. 5.

Referring now to FIGS. 5 and 6, another preferred embodiment of the patch is shown. The patch P has a centrally positioned medical grade foam 70, such as polyurethane foam which forms an "island" and is spaced by space or gap 72 which surrounds the foam 70 and spaces it from another layer of foam 74, preferably thinner than foam 70, which also surrounds foam 70. The gap 72 helps facilitate keeping oil 75 concentrated in foam 70 and not migrating to foam 74. Foam 74 can be a polyethylene or polyurethane foam. Foam 70 is preferably about 5 mm thick, in the range of 3 mm to 10 mm, whereas foam 74 is preferably about 3 mm thick, in the range of 1 mm to 3 mm. Since foam 70 is thicker than foam 74, it is compressed against the skin of the user during use which facilitates disbursement of the oil into the skin. Foam 70 absorbs liquid drug components such as oil 75. Foam 70 allows the drug to soak in quickly and also holds the drug until the foam 70 contacts the skin.

Foam 74 carries a layer of thin pressure sensitive medical grade adhesive (PSA) 77 which is about 2 mil thick. This thin foam 74 allows the bandage or patch to stretch and remain intact during wear. The patch can be applied to different areas of the skin easily. The pressure sensitive adhesive 77 provides effective adhesive to adhere to skin for the desirable length of wear time (such as 4 hours, 8 hours, 24 hours, etc.).

A release liner 76 is used to cover and protect the adhesive surface 77 before the adhesive contacts the skin. The liner extends beyond the edge of foam 74 to facilitate peeling the release liner from the foam. The liner can be made of silicone coated LDPE and is preferable 2 mils thick. Liner 76 also acts as a barrier to keep the oil in the patch during storage. If it was any other type of material, the oil would soak thru and be minimized/lost over time in storage.

A polyurethane (PU) film or tape 80 with an adhesive coating 78 on the bottom side of film 80 adheres the film 80 to the two foams 70, 74, on an opposite side of the foams from the release liner. The PU film 80 connects foams 70, 74 together. An additional benefit of the PU film is the "breathability" of the material to hold in the oil, but allow human perspiration to pass out, thus keeping the skin somewhat in control during long term use. Film 80 remains attached to foam 70, 74 during use of the patch.

The outer dimension of the liner 76 is preferably 2.5 inches×2.5 inches. The foam island 70 preferably has a diameter D1 of preferably 1 (one) inch while the gap 72 is about ⅛ inches and has a diameter D2 of about 1.250 inches. Outer edges of foam 74 preferably have a radius R1 of 0.500 inches, while outer corners of release liner 76 have a radius R2 of about 0.750 inches. Of course, other dimensions are contemplated by this disclosure. Beyond aesthetics, the rounded outer corners protect the patch from lifting at the corners during prolonged use.

In accordance with one embodiment of the disclosure, the patch is oil loadable and is designed to load and deliver oil to human skin. Liquid agents other than oils may also be used with the patch product.

In accordance with a preferred embodiment of the disclosure, the center of the patch (foam 70) is a circular polyurethane foam island capable of absorbing up to 500 mg of higher viscosity oils (or 300 mg for lower viscosity oils). The top layer of the patch is a comfortable polyurethane film tape 80, while the outer ring of the patch is a flexible, polyethylene or polyurethane foam tape 74, which provides optimal comfort and skin adhesion. The outer dimension of the patch (i.e., foam 74) is preferably 2 inches×2 inches with ½ inch rounded corners. All components are of medical grade quality and manufactured to ISO 13485:2016 compliance.

Another embodiment of the disclosure provides that the following oils can be used as oil 75: Cannabis oil (CBD, THC, CBG, CBN . . . ); Essential oils (lavender, peppermint . . . ); and Bio-Oils® as well as other suitable liquid agents.

Enhancers are commonly mixed with oils to improve skin absorption. The foam island is made of a highly absorbable polyurethane foam, which will degrade when exposed to certain chemistries. It is important to know which enhancers are and which are not suitable for use with the oil loadable patch. It is highly recommended that any mixture be verified safe and compatible with all of the patch materials before subjecting to users. Some suitable enhancer selections are: Alcohol types of solvents, such as, but not limited to, isopropanol, ethanol, methanol, menthol, n-propanol, propylene glycol, dipropylene glycol should have minimal to no effect on the polyurethane foam island; individual components, such as oleic acid, are safe enhancers to use; long chain oils, such as olive oil, rose oil, coconut oil, may be safe enhancers to use; enhancers called "oil", such as eucalyptus oil, are a "mixture" of components, not one single long chain oil component. Some of these oils would need to be verified as safe to use with the patch.

Enhancer types such as, but not limited to, DMSO, NMP, DMF, THF, m-cresol, toluene, methyl ethyl ketone, and acetone, are not suitable for this patch application and must not be used in any way. These enhancer types will degrade the polyurethane foam island; an enhancer compatibility study must be configured with the polyurethane foam island before it is mixed with active components and subjected to use and sale.

Referring as an example to FIGS. 5 and 6, to use the patch the following steps are performed. First, the clear plastic release liner 76 is removed on the "skin" side of the patch, thus exposing adhesive layer or member 77. The desired amount of oil 75 is then loaded onto the center circular polyurethane foam island 70; the clear plastic release liner 76 is reapplied for future use, or after about 3 seconds for oil to soak into circular foam island 70. The release liner is removed, and the patch is applied and adhered to skin via adhesive layer or member 77 formed on foam 74. Gentle hand pressure is applied to the patch for about 3 to 5 seconds. The patch is preferably applied to soft skin areas such as upper chest, hip area, or other hair free areas for application (the area may be shaved where needed).

The present disclosure allows the manufacturer, or individual users to dispense the drug components onto the absorbable foam. This foam can absorb in the range of 5 mg to 500 mg amount of drug or active ingredient (topical nutraceuticals, vitamins, etc.). This provides flexibility of drug dosage. The drugs do not need to be loaded before the adhesive layers are made.

An unloaded patch may be stored in a cool, dry area for up to 2 years; A loaded patch may be stored based on shelf life of the oil used, but no more than 2 years.

Individual users can dispense over-the-counter drugs at home or health care facilities. The manufacturer can dispense the drugs right before packaging, instead of dispensing drugs before patch assembling and converting. This greatly reduces the manufacturing scrap rates and complexity.

The "drugs" loaded here can be any liquid components such as but not limited to, as long as they do not dissolve the absorbent foam. The drugs can be oils (cannabis oils, tree oils, lavender oil, myrrh oil, sage oil, etc.) or vitamin D with enhancers, lidocaine with enhancers, estradiol with enhancers etc.

Many liquid components will evaporate during the heating process and impact final dose levels. Some drugs are not thermally stable and may convert to different chemical structures and affect efficacy. To avoid these problems in the present disclosure allows the drugs to be loaded directly onto the patches. Moreover, there is no heat involved in the process. This enables precise dosing and avoids thermal stability issues.

In accordance with another embodiment of the disclosure, the patch may be manufactured on a converter machine having separate rollers. That is, a first roller has a roll of patches, and the second roller has a roll of release liners which are applied onto the patches as they leave the first roller with an oil dispensing step in between. Alternatively, the release liner and oil may be manually applied to the patches.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by this disclosure and the appended claims.

The invention claimed is:

1. A transdermal patch for delivering a liquid drug to a user's skin, comprising:
    a first foam member which absorbs and retains said liquid drug until said first foam member contacts the user's skin;
    a second foam member positioned around said first foam member,
    wherein a gap is formed between said first foam member and said second foam member and surrounds said first foam member;
    a film member which has a first portion which extends across a surface of said first foam member and a second portion which extends across a surface of said second foam member and thereby connects said first foam member and said second foam member; and
    wherein said first foam member has a first thickness which is greater than a second thickness of said second foam member;
    wherein said first foam member extends beyond an outer surface end of second portion of said film member.

2. The transdermal patch of claim 1, wherein said first foam member comprises a polyurethane foam.

3. The transdermal patch of claim 1, wherein said second foam member comprises one of polyethylene foam and polyurethane foam.

4. The transdermal patch of claim 1, wherein said first foam member has a thickness in the range of 5 mm to 10 mm.

5. The transdermal patch of claim 1, wherein said second foam member has a thickness in the range of 1 mm to 3 mm.

6. The transdermal patch of claim 1, wherein said film member further comprises an adhesive coating which covers said at least one of first foam member and said second foam member.

7. The transdermal patch of claim 6, further comprising a release liner extending across and covering said adhesive coating.

8. The transdermal patch of claim 1, wherein said first foam member absorbs up to 500 mg of liquid drug.

* * * * *